(12) United States Patent
Prather

(10) Patent No.: US 12,121,653 B2
(45) Date of Patent: Oct. 22, 2024

(54) WEARABLE INTRANASAL CLIP APPARATUS AND METHOD OF USE

(71) Applicant: Nathan T. Prather, Kansas City, MO (US)

(72) Inventor: Nathan T. Prather, Kansas City, MO (US)

(73) Assignee: Nathan T. Prather, Kansas City, MO (US)

( * ) Notice: Subject to any disclaimer, the term of this patent is extended or adjusted under 35 U.S.C. 154(b) by 884 days.

(21) Appl. No.: 17/186,869

(22) Filed: Feb. 26, 2021

(65) Prior Publication Data

US 2021/0236753 A1 Aug. 5, 2021

Related U.S. Application Data

(63) Continuation-in-part of application No. 16/173,819, filed on Oct. 29, 2018, now abandoned.

(60) Provisional application No. 62/625,551, filed on Feb. 2, 2018.

(51) Int. Cl.
| | |
|---|---|
| *A61M 15/08* | (2006.01) |
| *A61L 9/03* | (2006.01) |
| *A61M 15/00* | (2006.01) |
| *A61M 21/00* | (2006.01) |

(52) U.S. Cl.
CPC .............. *A61M 15/08* (2013.01); *A61L 9/037* (2013.01); *A61M 15/0028* (2013.01); *A61M 2021/0016* (2013.01)

(58) Field of Classification Search
CPC .............. A61M 15/00; A61M 21/00; A61M 2021/0011; A61M 15/08; A61M 2021/0016; A61M 21/02; A61M 15/085; A61M 2209/088
See application file for complete search history.

(56) References Cited

U.S. PATENT DOCUMENTS

| | | |
|---|---|---|
| 3,758,950 A | 9/1973 | Krouzian |
| D242,828 S | 12/1976 | Lahay |
| D287,166 S | 12/1986 | Lipsky et al. |
| D350,311 S | 9/1994 | Willis et al. |
| D350,499 S | 9/1994 | Willis et al. |
| 7,048,953 B2 | 5/2006 | Vail, III et al. |
| 7,108,198 B2 | 9/2006 | Altadonna, Jr. |
| 7,150,888 B1 | 12/2006 | Vail, III et al. |
| 7,318,438 B2 | 1/2008 | Brown |
| 7,837,649 B1 | 11/2010 | Aboff |
| D683,016 S | 5/2013 | Mirza et al. |
| 9,272,117 B2 | 3/2016 | Miledi |
| D878,549 S | 3/2020 | Wilson et al. |
| D908,209 S | 1/2021 | Ronayne et al. |
| D916,276 S | 4/2021 | Wilson et al. |

(Continued)

*Primary Examiner* — Jason E Flick

(74) *Attorney, Agent, or Firm* — HOVEY WILLIAMS LLP

(57) ABSTRACT

A wearable intranasal device that dispenses concentrated oils, specifically Aromatherapy and Cannabidiol or CBD, allowing each to evaporate naturally through the nasal cavity providing temporary relief of a variety of symptoms these products have been positively found to impact. The device is a single unit consisting of two barrels on both ends joined by a bridging center arch and which will hug the septum of the user ergonomically not causing any irritation to the user. Each barrel receives a cotton wick which will hold the concentrated oil(s).

9 Claims, 7 Drawing Sheets

(56) References Cited

U.S. PATENT DOCUMENTS

| | | |
|---|---|---|
| 2008/0023007 A1 | 1/2008 | Dolezal et al. |
| 2009/0054923 A1 | 2/2009 | Benson |
| 2010/0147300 A1* | 6/2010 | Lorenzati .......... A61M 15/0028 |
| | | 128/204.14 |
| 2015/0217064 A1 | 8/2015 | Trzecieski |
| 2015/0250973 A1* | 9/2015 | Allum ................ A61M 16/201 |
| | | 128/205.25 |

* cited by examiner

WEARABLE INTRANASAL CLIP APPARATUS AND METHOD OF USE

CROSS-REFERENCE TO RELATED APPLICATION

This application is a Continuation-in-Part of U.S. Nonprovisional patent application Ser. No. 16/173,819 filed Oct. 29, 2018, which claims priority in U.S. Provisional Patent Application No. 62/625,551 filed Feb. 2, 2018, which are incorporated herein by reference.

BACKGROUND OF THE INVENTION

1. Field of the Invention

The present invention relates generally to a wearable nasal device and method for use thereof, and more specifically to a wearable intranasal filtration and inhaling device that extracts toxins and pollutants from the outside air while dispensing concentrated Essential oil(s), Cannabidiol (CBD) and/or any other inhalant, medical or nonmedical, in order to provide clean and therapeutic benefits to the consumer.

2. Description of the Related Art

Aromatherapy's roots can be traced back more than 3,500 years when the first users burnt aromatic herbs to assist in treatment of their ill or to relax their dying. Since that time, the process has been refined through science to capture the oils of different raw plant materials including but not limited to flowers, fruits, leaves, wood, bark, peel and seeds. The oils are extracted through the processes of distillation (the extraction of the essential meaning or most important aspects of something by a process of heating and cooling), hydrodistillation (a variant of steam and distillation in which material is soaked for some time in water and after with the mixture is heated and volatile materials are carried away in steam, condensed and separated) and expression (the production of something, especially by pressing or squeezing it out). Essential Oils, when inhaled through the nostrils, are absorbed immediately into the olfactory nerve, then to the brain which impacts the amygdala, a part of the limbic system that coordinates with the user's neural network and manages certain aspects of emotion and memory. Lemon Oils have been known to stimulate appetite, energize, and purify. Lavender Oil is used to calm anxiety, relax or decrease general discomfort, assist the consumer to fall asleep and have a more restful sleep. Peppermint Oil can energize, ease motion sickness, aid heartburn, alleviate tension or simply clear sinus congestion. Tests around the world have shown Essential Oils to help manage a variety of symptoms including but not limited to food cravings, anxiety, increased memory and alertness. While consumers claim that certain essential oils assist with the pain of headaches, migraines, allergies, insomnia, depression and nausea. Other testimonials show increased blood flow which could serve as a natural aphrodisiac. The reliefs or benefits that have been listed only encompass a few Essential Oils, which is an emerging market to say the least. Global market size is estimated in 2020 to reach USD $5.2 Billion and is expected to increase to USD $14.1 Billion by 2026. This invention has been created to provide a safe, filtered, concentrated and proven method of inhalation for the consumer.

Cannabidiol (CBD) roots can be traced back to the 19th century assisting Queen Victoria with her menstrual cramps. This is not to be confused with tetrahydrocannabinol (THC) which provides the "high" sensation; rather, CBD is a chemical compound in the cannabis plant that provides a relaxing state to the user. There are three processes of extraction, CO2 extraction (using carbon dioxide under high pressure and extremely low temperatures to isolate, preserve and maintain the purity of the medicinal oil), Ethanol (high grade grain alcohol used to create high quality cannabis oil appropriate for vape pen cartridges and other similar products) and Olive Oil (a safe and inexpensive way to extract cannabis oil but creates a perishable substance). CBD was first successfully found to assist with epilepsy; however, with further research it has been identified as the responsible component for medical marijuana's benefits, including but not limited to; cigarette addiction, acne, diabetes, multiple sclerosis, rheumatoid arthritis and other chronic pain conditions. Cannabidiol assists with these ailments by reducing inflammation, increasing insulin production and regulating the immune system to provide a better way of life for the consumer. CBD is an emerging market with a global share in 2020 of USD $968 Million and estimated to increase to USD $5.3 Billion by 2025. This invention has been created to provide a safe, filtered, concentrated and proven method of inhalation for the consumer.

Essential Oils and Cannabidiol (CBD) have been proven through lab tests, clinical trials and user testimonials to provide a better way of life for the people who use them. Similar products are in the marketplace; however, none offer the benefits this product does by natural evaporation of these oils through natural respiration. It has been documented in studies worldwide, the user population and demand for these products is increasing due to the latest research of inhaling these types of oils and the overall benefits that they provide which will no doubt increase along with the Global Market. The demand is in place for a product that safely emits the vapors for both of types of oil to be absorbed naturally in the nasal passages while the consumer simply breathes. Creating a wearable intranasal filtration and inhalation device provides the consumer therapeutic relief from irritating symptoms and provides the ability for a consumer to focus or create mood enhancement that can lead to an overall better way of life for the individual.

Heretofore there has not been available a system or method for a wearable intranasal device with the advantages and features of the present invention.

BRIEF SUMMARY OF THE INVENTION

The present invention generally provides a wearable intranasal filtration and inhaling device that extracts toxins and pollutants from the outside air while dispensing concentrated Essential oil(s), Cannabidiol (CBD) and/or any other inhalant, medical or nonmedical which evaporate naturally through the nasal cavity providing therapeutic benefits these products have been positively found to impact while offering the user an aromatic and pleasant scent. The device, made from a polycarbonate styrene plastic resin, is one unit, made up of five (5) parts; consisting of two barrels/pods one on each end, containing a cotton wick. Once the wick is inserted into the base pod, the cap or top of the barrel/pod, will snap on the energy director, which is the small lip at the tip of the lower barrel/pod that is part of the arch/bridge. The cap and barrel will be ultrasonically welded by sending a frequency through the device to the energy director causing it to collapse and weld both cap and pod together as one unit locking the wick in place and creating one solid unit. The wick serves two purposes, first, to filter out toxins, contaminates, pollutants or any other unpleasantries of the outside air and second, to hold the concentrated essential oil(s), CBD and/or any other inhalant (s), medical or nonmedical, gradually releasing vapors into the consumers nasal cavity. Each barrel/pod will have ventilation holes located at the top and bottom in order to provide superior filtration and ventilation, granting outside air to flow around and through the device to lessen the concentration of the oil(s)/medicines in the user's nasal cavity. The barrels are supported or bridged together by a flexible polycarbonate plastic center piece (the arch/bridge) that is malleable enough for each consumer to fit the device comfortably hugging their septum and positioning each barrel/pod ergonomically into each nostril.

BRIEF DESCRIPTION OF THE DRAWINGS

The drawings constitute a part of this specification and include exemplary embodiments of the present invention illustrating various objects and features thereof.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

II. Preferred Embodiment Intranasal Device System 2

Figure 1:
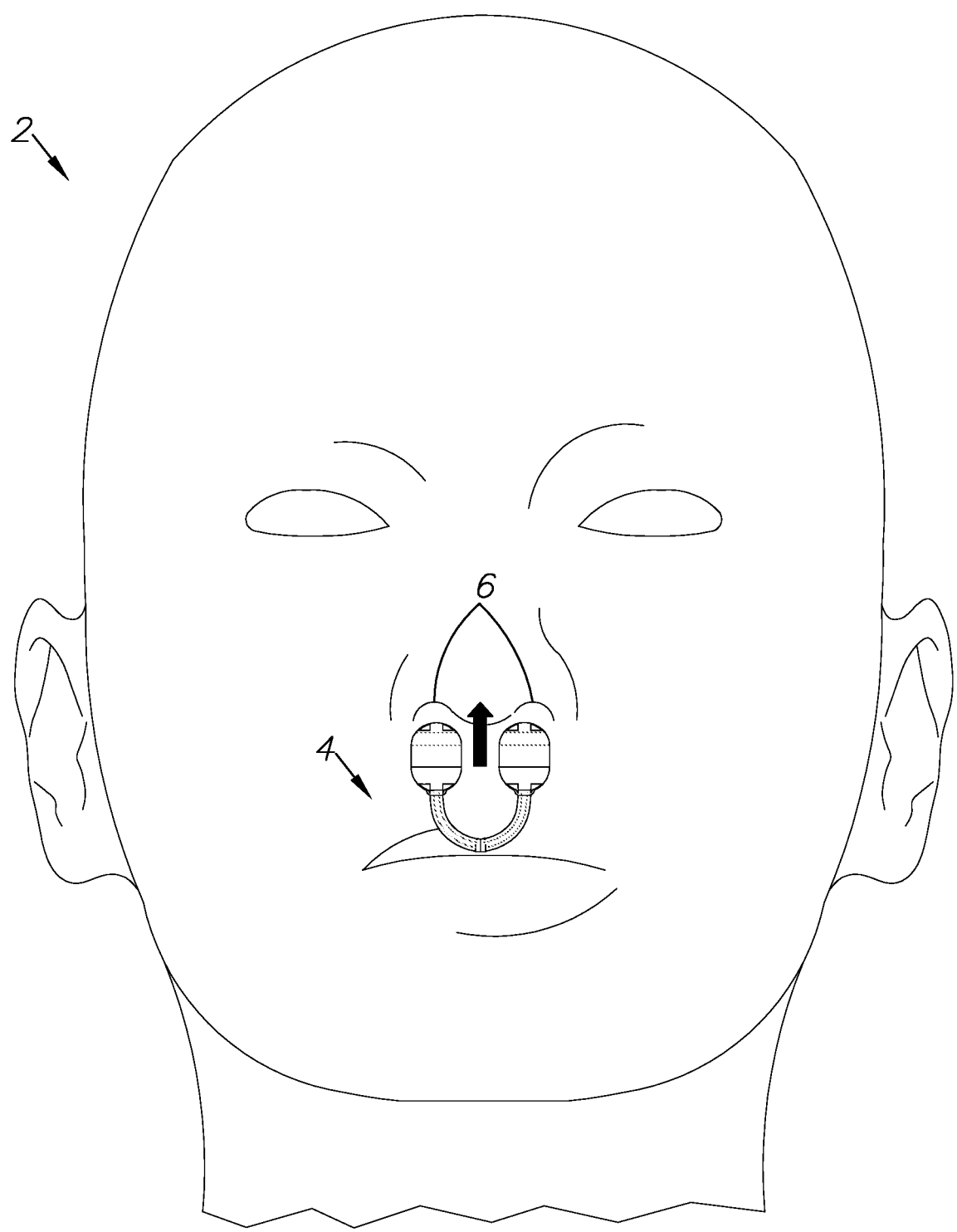
FIG. 1 is a front elevational view of a preferred embodiment of the present invention shown in a typical environment.

FIG. 1 shows an intranasal device system 2 where a wearable intranasal device 4 is deployed within the nostrils 6 of a user. This allows for the delivery of evaporating oils, such as aromatherapy and/or cannabinol (CBD) oils, into the nasal cavities of the user.

Figure 2:
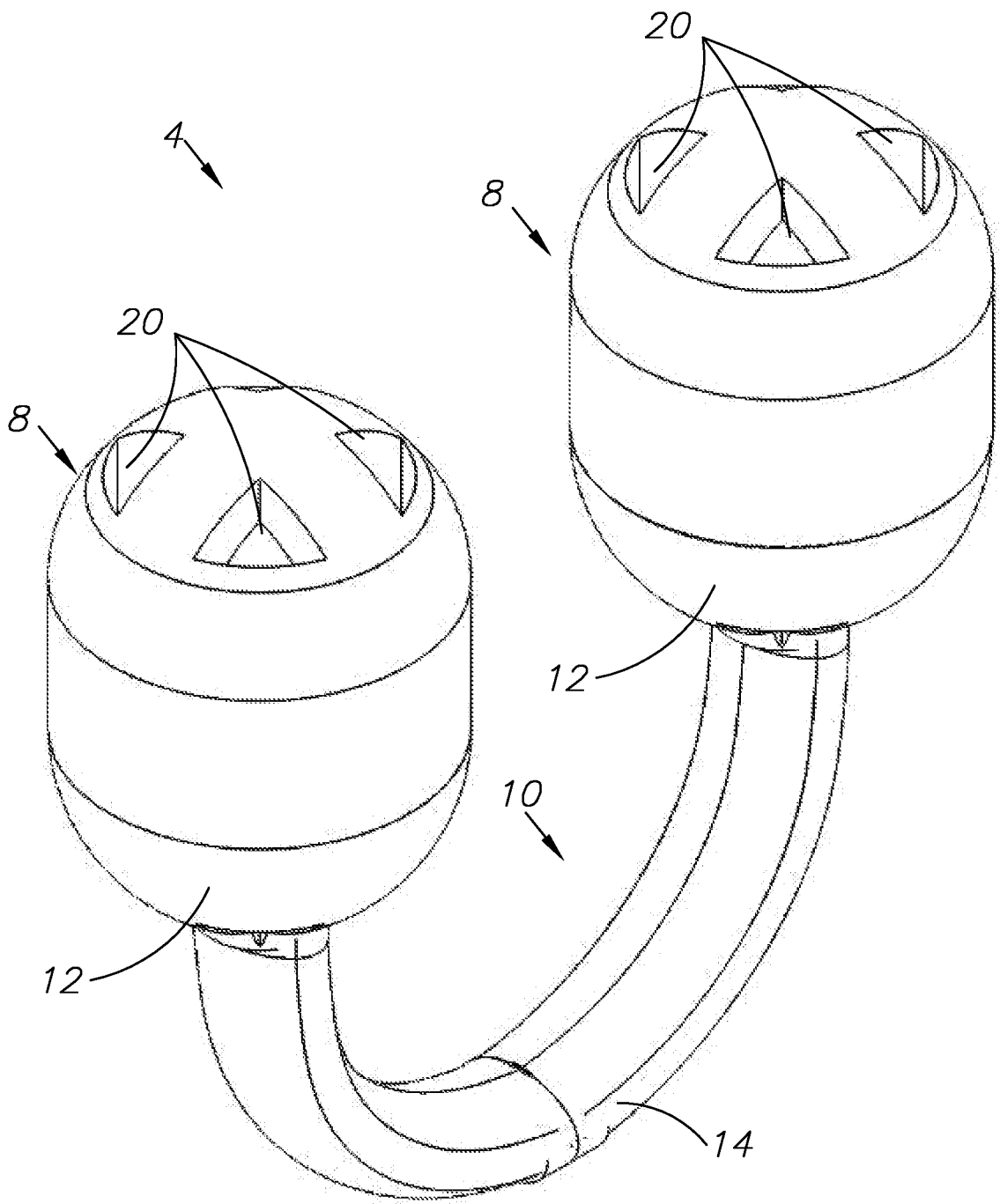
FIG. 2 is a three-dimensional isometric view thereof shown in isolation.
Figure 5:
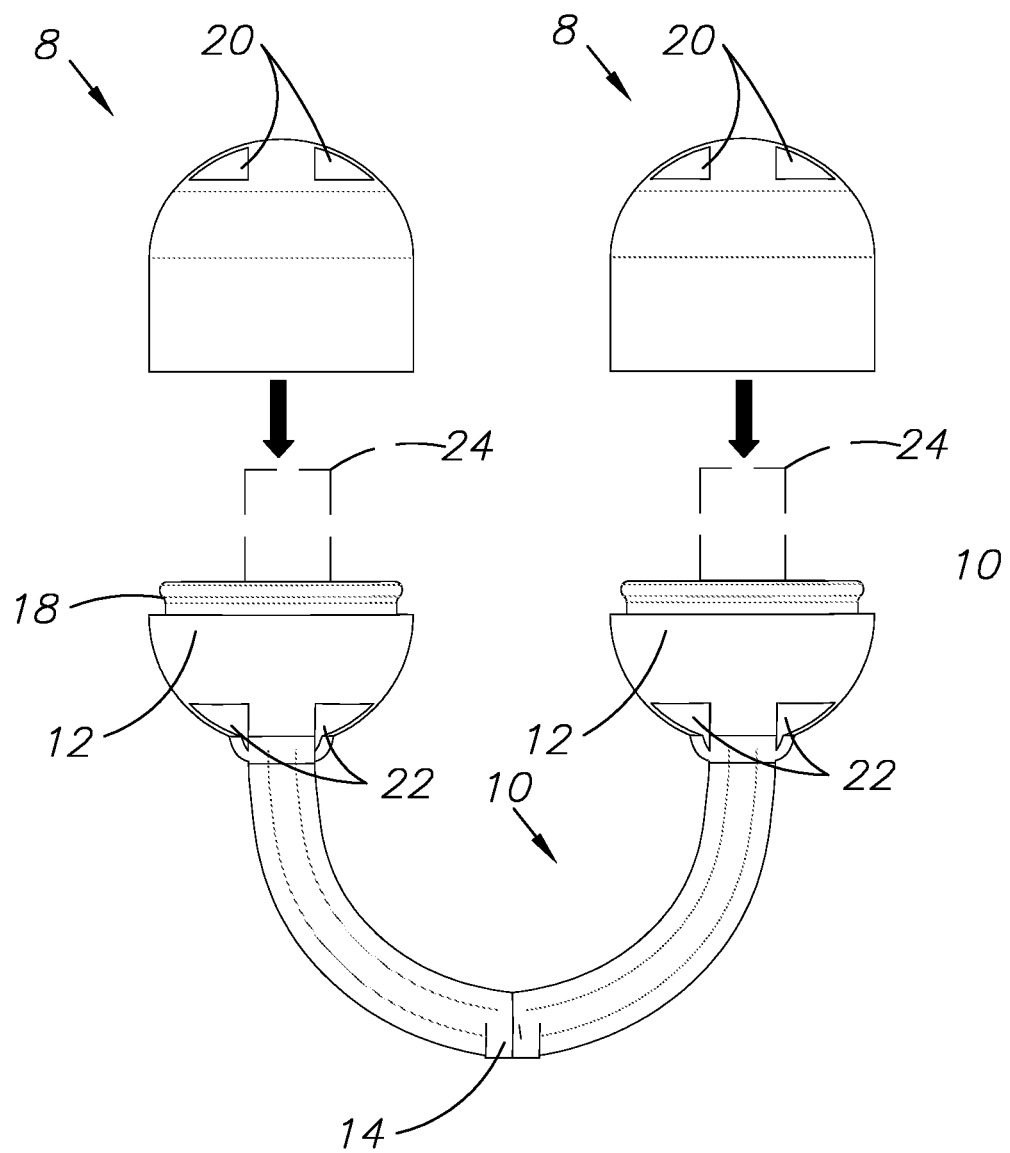
FIG. 5 is a front elevational view thereof showing the top barrel elements being fitted to the bottom portion thereof.

As shown in FIG. 2, the intranasal device 4 generally includes a bottom portion 10 and a pair of top barrel portions 8. The bottom portion 10 includes two bottom barrel portions 12 joined by a bridging arch 14. The top barrel portions 8 include ventilation holes 20 for providing ventilation into the wick 24 stored between the top 8 and bottom 12 barrel portions as shown in FIG. 5. The bottom barrel portions 12 similarly have corresponding ventilation holes 22.

Figure 3:
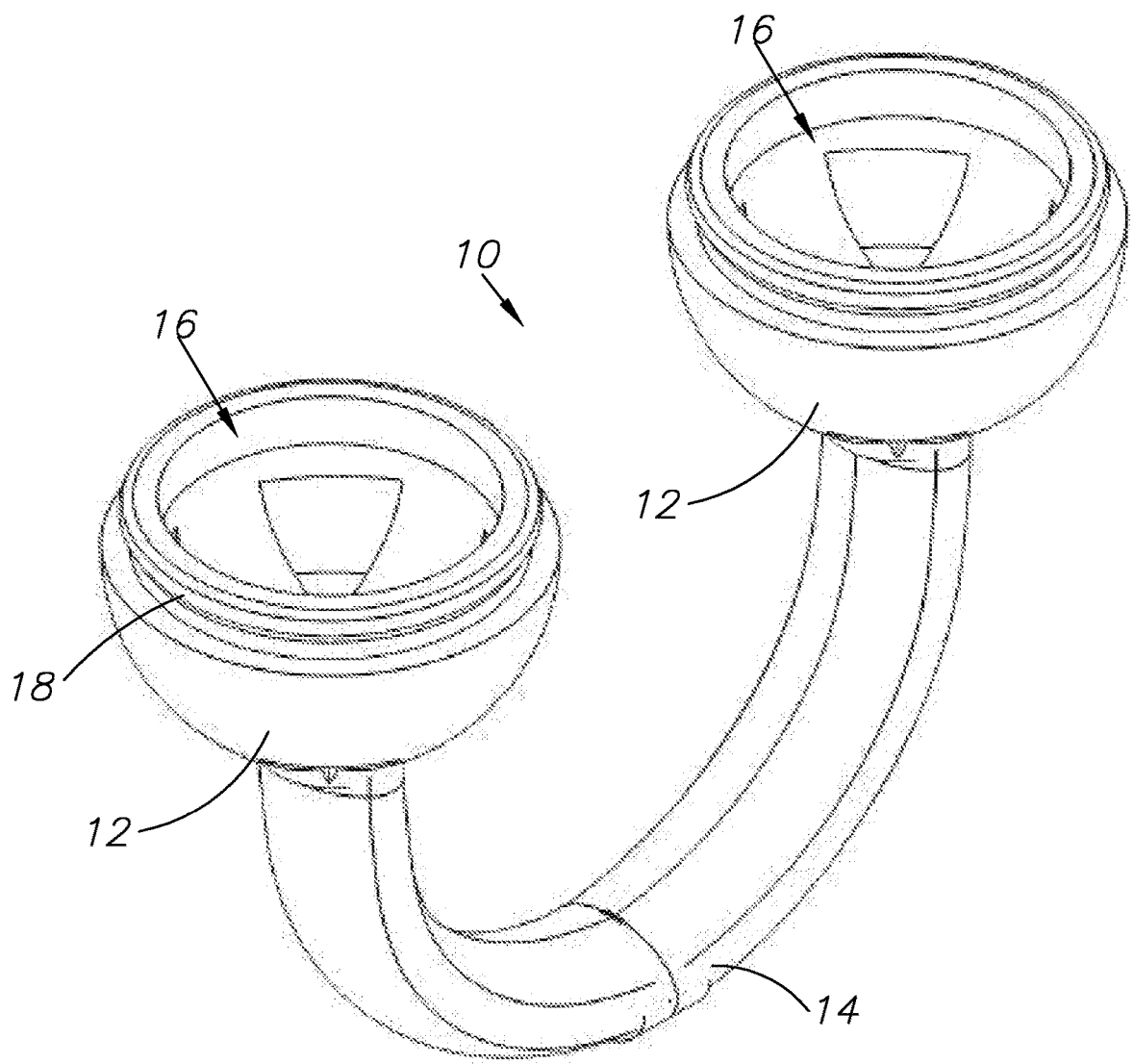
FIG. 3 is a three-dimensional isometric view of a bottom portion of the embodiment thereof including bottom barrel portions and bridging arch.
Figure 4:
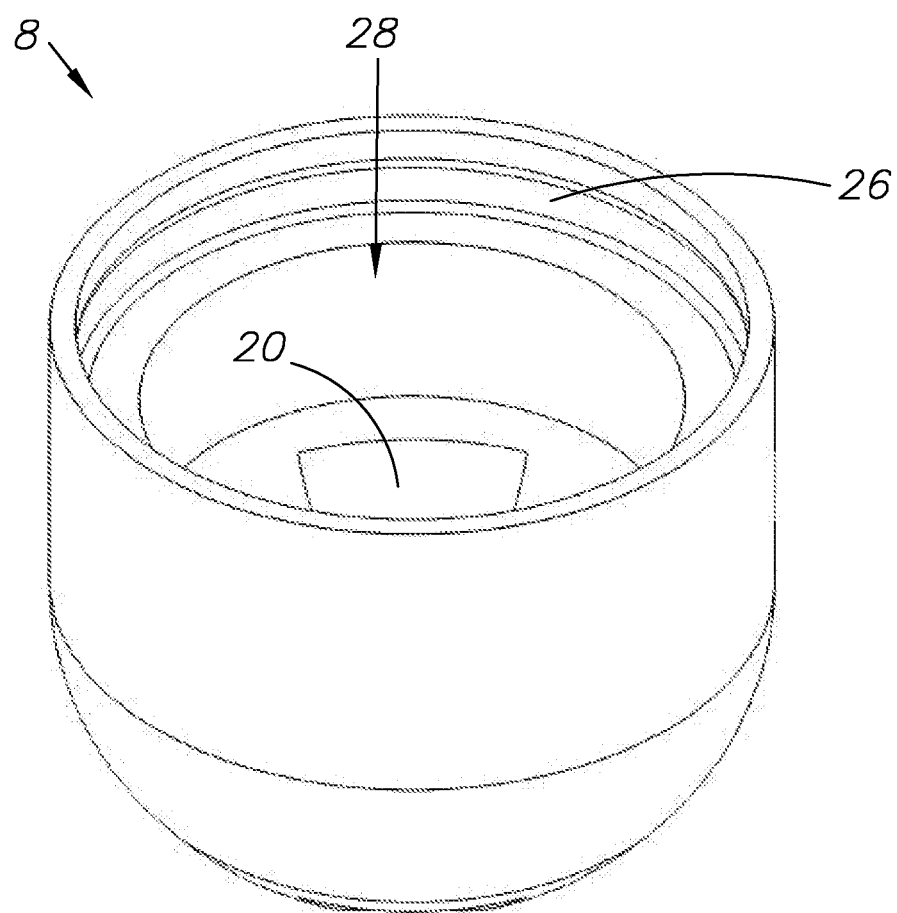
FIG. 4 is a three-dimensional isometric view of a top barrel element thereof.

As shown in FIG. 3, the bottom barrel portions 12 include an internal cavity 16 for receiving the wick 24 which contains the oils for delivery to the user. A connector ring 18 allows for the locking onto the bottom barrel portion 12 of the top barrel portion 8 which, as shown in FIG. 4, includes a corresponding connector lip 26. The top barrel portion 8 also includes a corresponding internal cavity 28 for receiving the wick. In addition to containing oils or other aromatherapeutic scents or elements, the wick can serve to filter toxins and other unpleasant or undesirable fumes from the air before entering the user's airway.

The intranasal device 4 is preferably molded of bisphenol A-free (BPA-free) plastic or similar resin, a non-irritating plastic that is flexible and non-corrosive with the use of concentrated oils. When worn, very little of the intranasal clip will show. As indicated in FIG. 1 only the arch 14 that joins the two barrels will be visible.

Each of the barrels can be opened to insert aroma wicks containing the oils. The barrels include openings to allow vapors from the oils to be inhaled into the nose. The dosages may vary depending on the requirements of the user.

Figure 6:
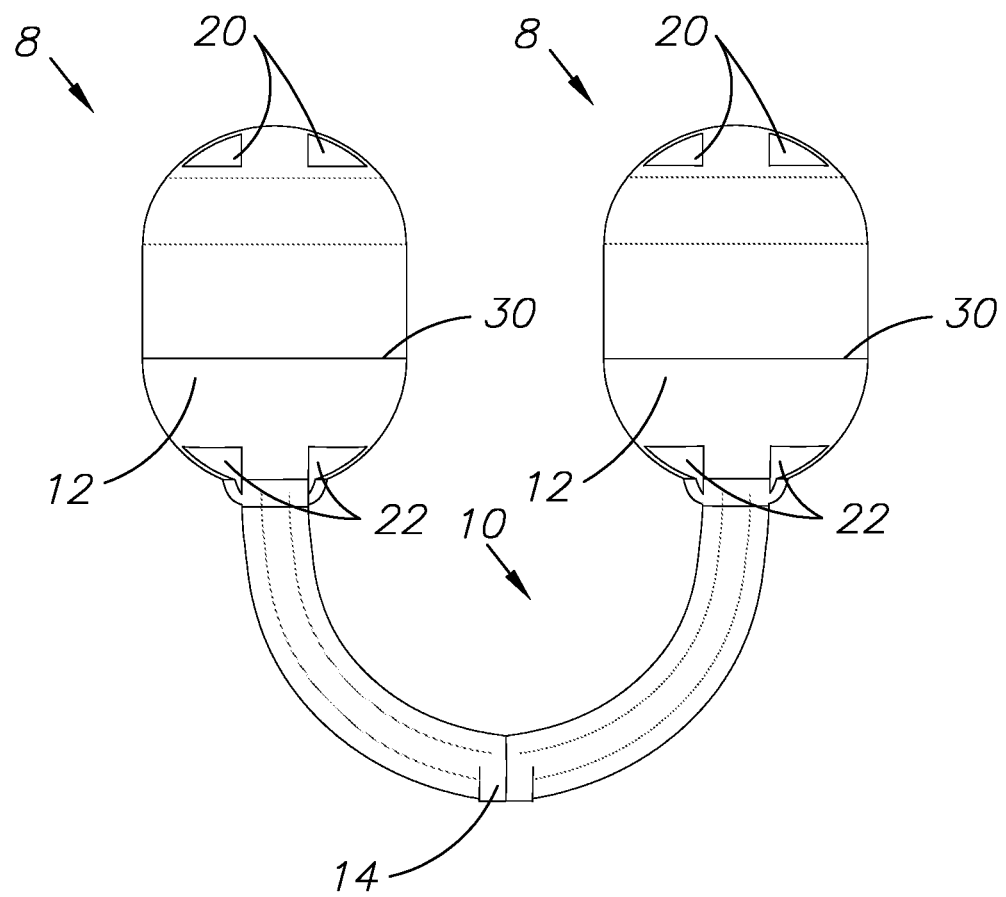
FIG. 6 is a front elevational view thereof shown in a fully assembled orientation.
Figure 7:
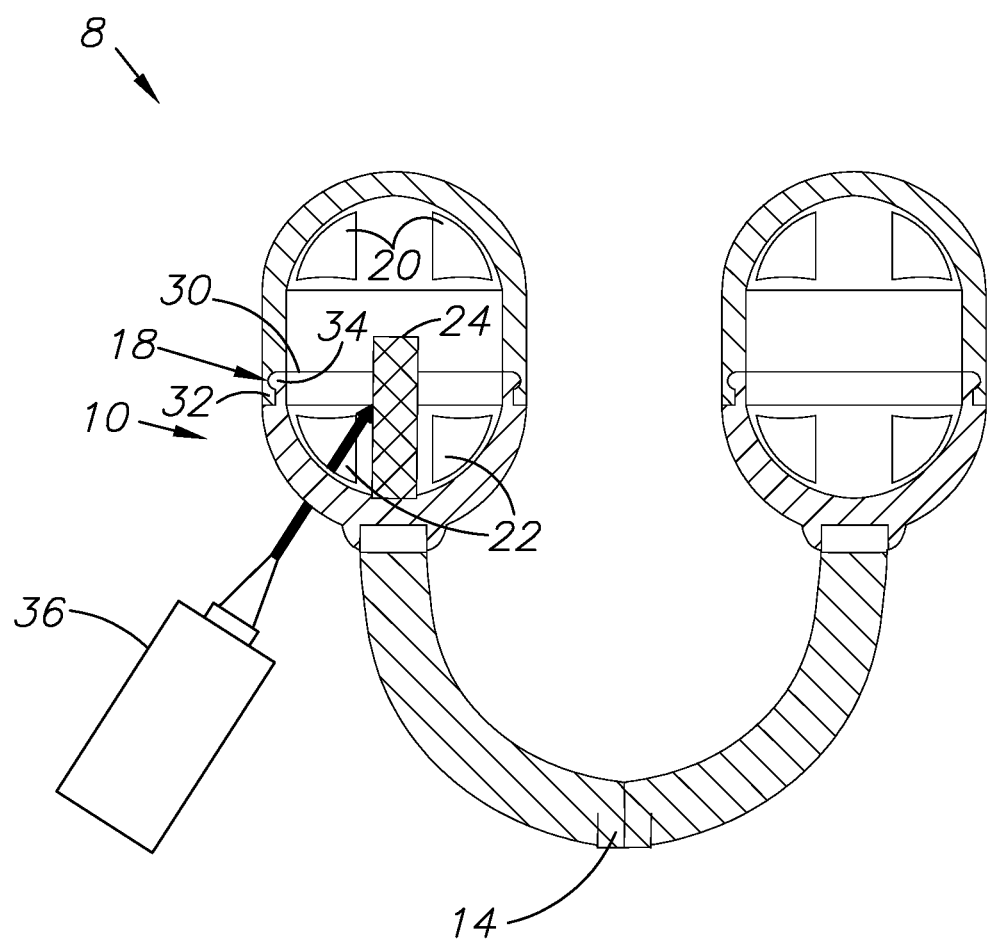
FIG. 7 is a front sectional view taken about the centerline of the embodiment shown in FIGS. 1-6.

FIG. 7 shows an alternative embodiment, wherein the barrel has been ultrasonically welded about the butt joint formed between the top barrel portion 8 and the bottom portion 10 of the barrel via the connector ring. A lower horn 34 and upper horn 32 snap together and then the two portions are ultrasonically welded about the weld line 30, also shown on FIG. 6. This prevents the barrel from being opened, removing the possibility that the top barrel portion 8 will be retained within the user's nostril when the user attempts to remove the intranasal device system.

FIG. 7 also shows how a wick 24 can be refilled while placed within the barrel internal cavity 28 via the ventilation holes 20, 22 without requiring the removal of the top barrel portion 8. A pipette or dropper 36 can be used to add oils or other scented liquid to the wick to recharge it.

It is to be understood that while certain embodiments and/or aspects of the invention have been shown and described, the invention is not limited thereto and encompasses various other embodiments and aspects.

Having thus described the invention, what is claimed as new and desired to be secured by Letters Patent is:

1. A wearable intranasal oil delivery system comprising:
a pair of barrel chambers joined by a bridging arch, each of said barrel chambers configured to be inserted into a respective cavity and comprising a bottom portion that is dome shaped and a top portion that is dome shaped and extending away from the bottom portion;
each respective one of said barrel chambers is affixed to a respective end of said bridging arch such that each respective one of said barrel chambers extends vertically upward from said respective end of said bridging arch, and said bridging arch extends vertically downward when each of said barrel chambers is inserted into said respective cavity so that a bottom most point of said bridging arch is below a bottom most point of each of said barrel chambers;
wherein said top portion of each respective barrel chamber is connected to said bottom portion of each respective barrel chamber via an interlocking upper horn of each said respective top portion and a lower horn of each respective bottom portion;

each of said barrel chambers comprising an internal cavity storing a wick;

each of said barrel chambers comprising a plurality of ventilation holes for delivering aroma from said wick into said respective cavity.

2. The system of claim 1, wherein said wick contains oils.

3. The system of claim 2, wherein said oils comprise aromatherapy oils.

4. The system of claim 2, wherein said oils comprise Cannabidiol oils.

5. The system of claim 1, wherein:

said bottom portion of each of said barrel chambers comprises a receiver ring;

said top portion of each of said barrel chambers comprises a locking ring; and said receiver ring and said locking ring are configured to releasably join said top portion and said bottom portion of each of said barrel chambers.

6. The system of claim 5, wherein:

said top portion of each of said barrel chambers comprises a first set of said plurality of ventilation holes; and said bottom portion of each of said barrel chambers comprises a second set of said plurality of ventilation holes.

7. The system of claim 6, wherein:

said first set of plurality of ventilation holes is located on a top face of said top portion of each of said barrel chambers; and said second set of plurality of ventilation holes is located on a bottom face of said bottom portion of each of said barrel chambers.

8. The system of claim 1, wherein said wick is configured to filter air drawn through said plurality of ventilation holes.

9. A wearable intranasal oil delivery system comprising:

a pair of barrels for inserting into nasal cavities, each of said pair of barrels comprising:

a dome-shaped bottom portion having a bottom surface defining a bottom convex profile and a lower horn positioned above the bottom surface, and a dome-shaped top portion having a top surface defining a top convex profile and an upper horn positioned below the top surface, the upper horn interlocking with said lower horn of said bottom portion to connect said top portion to said bottom portion and defining an internal cavity;

a bridging arch connected to said bottom surface of said bottom portion of each of said pair of barrels and extending downwardly so that a bottom most point of said bridging arch is below a bottom most point of said bottom portion of each of said pair of barrels when said pair of barrels are inserted into said nasal cavities; and a pair of wicks positioned inside said internal cavity of each of said pair of barrels, wherein each of said pair of barrels comprises a plurality of ventilation holes for delivering aroma from said pair of wicks into said nasal cavities.

\* \* \* \* \*